(12) United States Patent
Franks et al.

(10) Patent No.: US 6,274,633 B1
(45) Date of Patent: Aug. 14, 2001

(54) NMDA ANTAGONIST

(75) Inventors: Nicholas Peter Franks; Mervyn Maze, both of London (GB)

(73) Assignee: Imperial College of Science, Technology, and Medicine, London (GB)

( * ) Notice: Subject to any disclaimer, the term of this patent is extended or adjusted under 35 U.S.C. 154(b) by 0 days.

(21) Appl. No.: 09/378,806

(22) Filed: Aug. 23, 1999

(30) Foreign Application Priority Data

Jul. 29, 1999 (GB) .................................................. 9917822

(51) Int. Cl.⁷ .................................................. A61K 33/00
(52) U.S. Cl. .......................... 514/769; 424/600; 514/816; 514/959; 514/220; 514/759; 514/731; 514/812
(58) Field of Search ............................ 424/600; 514/769, 514/220, 816, 959, 759, 731, 812

(56) References Cited

PUBLICATIONS

Franks et al, "How does xenon produce anaesthesia?", Nature, vol. 396, p. 324, Nov. 1998.*
Bekkers, J.M., and Stevens, C.F., Proc. Natl. Acad. Sci. USA 88: 7834–7838 (1991).
Brockmeyer, D.M., and Kendig, J.J., Br. J. Anaesthesia 74: 79–84 (1995).
Cullen, S.C., et al., Anesthesiology 31: 305–309 (1969).
Cullen, S.C., and Gross, E.G., Science 113:580–582 (1951).
Davies, J., et al., Neurosci. Lett. 21: 77–81 (1981).
Franks, N.P., and Lieb, W.R., Br. J. Anaesthesia 71: 65–76 (1993).
Franks, N.P., and Lieb, W.R., Nature 367: 607–614 (1994).
Franks, N.P., and Lieb, W.R., Anesthesiology 84: 716–720 (1996).
Goto, T., et al., Anesthesiology 86: 1273–1278 (1997).
Hadingham, K.L., et al., Proc. Natl. Acad. Sci. USA 89: 6378–6382 (1997).
Kennedy, R.R., et al., Anaesth. Intens. Care 20: 66–70 (1992).
Koblin, D.D., et al., Anesth. Anal. 87: 419–424 (1998).
Lachmann, B., et al., Lancet 335: 1413–1415 (1990).
Lawrence, J.H., et al., J. Physiol. 105: 197–204 (1946).
Luttropp, H.H., et al., Acta Anaesthesiol. Scand. 38: 121–125 (1994).
Mennerick, S., et al. J. Neurophysiology 73: 320–332 (1995).
Mihic, S.J., et al., Nature 389: 385–389 (1997).
Segal, M.M., and Furshpan, E.J., J. Neurophysiology 64: 1390–1399 (1990).
Smith, R.A., et al., Biochim. Biophys. Acta 645: 327–338 (1981).
Tanelian, D.L., et al., Anesthesiology 78: 757–776 (1993).
Watkins, J.C., and Evans, R.H., Ann. Rev. Pharmacol. Toxicol. 21: 165–204 (1981).
Weathersby, P.K., and Homer, L.D., Undersea Biomedical Res. 7: 277–296 (1980).
Whitehurst, S.L., J. Neurosurgical Anesthesiology 6: 275–279 (1994).
Wlaz, P., et al., Eur. J. Neuroscience 6: 1710–1719 (1994).

* cited by examiner

*Primary Examiner*—Frederick Krass
(74) *Attorney, Agent, or Firm*—Mary M. Krinsky

(57) ABSTRACT

The present invention relates to the use of xenon as an NMDA antagonist. In particular, the invention relates to a method of treatment comprising modulating the activity of an NMDA receptor in a mammal, the method comprising modulating the activity of the NMDA receptor by administering to the mammal a therapeutically effective amount of xenon. In a further aspect, the invention provides a process for the preparation of a pharmaceutical composition suitable for modulating the activity of an NMDA receptor.

10 Claims, 3 Drawing Sheets

NMDA ANTAGONIST

CROSS-REFERENCES TO RELATED APPLICATIONS

This application claims priority benefit under Title 35, United States Code §119 of United Kingdom application number 9917822.0 filed Jul 22, 1999.

STATEMENT REGARDING FEDERALLY SPONSORED RESEARCH

Not Applicable

BACKGROUND OF THE INVENTION

The present invention relates to a method of modulating the activity of NMDA receptors in a mammal. In particular, the invention relates to a new NMDA antagonist, and its use in the treatment of conditions associated with NMDA receptor activity.

The NMDA (N-methyl-D-aspartate) receptor is a major subclass of glutamate receptor and glutamate is believed to be the most important excitatory neurotransmitter in the mammalian central nervous system. Importantly, activation of the NMDA receptor has been shown to be the central event which leads to excitotoxicity and neuronal death in many disease states, as well as a result of hypoxia and ischaemia following head trauma, stroke and following cardiac arrest.

It is known in the art that the NMDA receptor plays a major role in the synaptic plasticity which underlies many higher cognitive functions, such as memory and learning, as well as in certain nociceptive pathways and in the perception of pain (Collingridge et al, The NMDA Receptor, Oxford University Press, 1994). In addition, certain properties of NMDA receptors suggest that they may be involved in the information-processing in the brain which underlies consciousness itself.

NMDA receptor antagonists are therapeutically valuable for a number of reasons, such as the following three specific reasons. Firstly, NMDA receptor antagonists confer profound analgesia, a highly desirable component of general anaesthesia and sedation. Secondly, NMDA receptor antagonists are neuroprotective under many clinically relevant circumstances (including ischemia, brain trauma, neuropathic pain states, and certain types of convulsions). Thirdly, NMDA receptor antagonists confer a valuable degree of amnesia.

However, it is clear from the prior art that there are a number of drawbacks associated with current NMDA receptor antagonists. These include the production of involuntary movements, stimulation of the sympathetic nervous system, induction of neurotoxicity at high doses (which is pertinent since NMDA receptor antagonists have low potencies as general anaesthetics), depression of the myocardium, and proconvulsions in some epileptogenic paradigms e.g., "kindling" (Wlaz P et al, Eur. J. Neurosci. 1994; 6:1710–1719). In particular, there have been considerable difficulties in developing new NMDA receptor antagonists that are able to cross the blood-brain barrier. This factor has also limited the therapeutic applications of many known NMDA antagonists.

The present invention thus seeks to provide an improved NMDA receptor antagonist for general pharmaceutical use which can readily diffuse across the blood brain barrier.

BRIEF SUMMARY OF THE INVENTION

This invention relates to the use of xenon as an NMDA antagonist. Encompassed by the invention are methods of treating mammals by modulating the activity of an NMDA receptor, and methods of modulting the activity of an NMDA receptor by administering to a mammal a therapeutically effective amount of xenon. Various aspects of the invention are presented in the following description and accompanying claims.

DETAILED DESCRIPTION OF THE INVENTION

Figure 1:
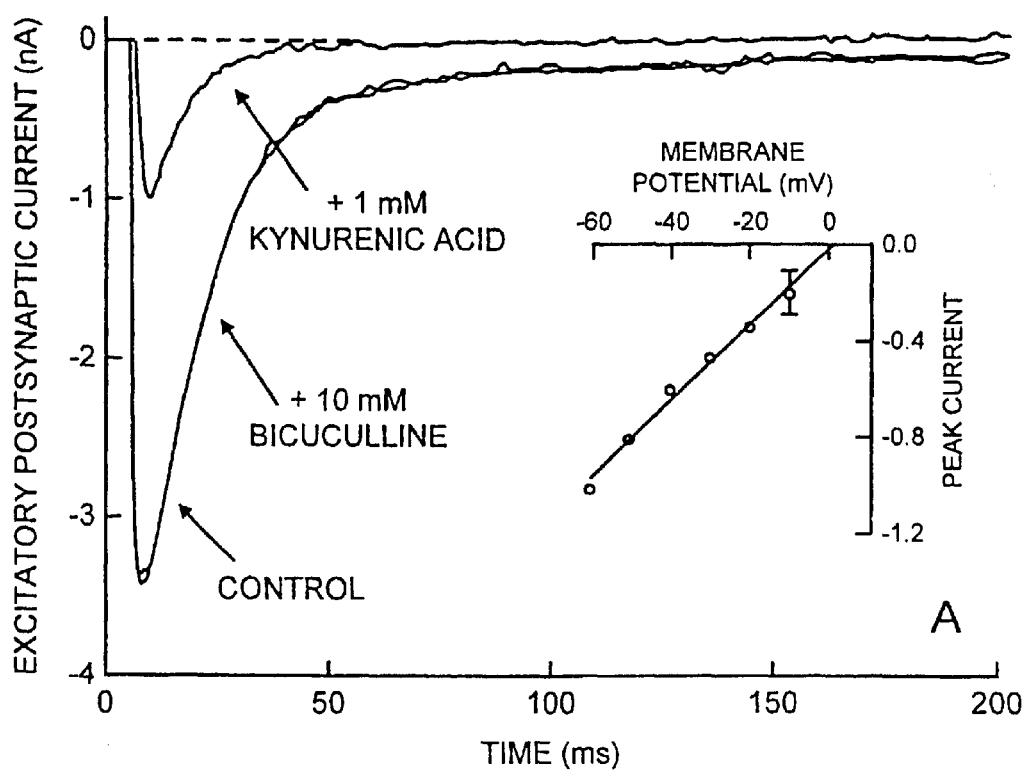
FIGS. 1A and B show control excitatory and inhibitory postsynaptic responses.
Figure 1:
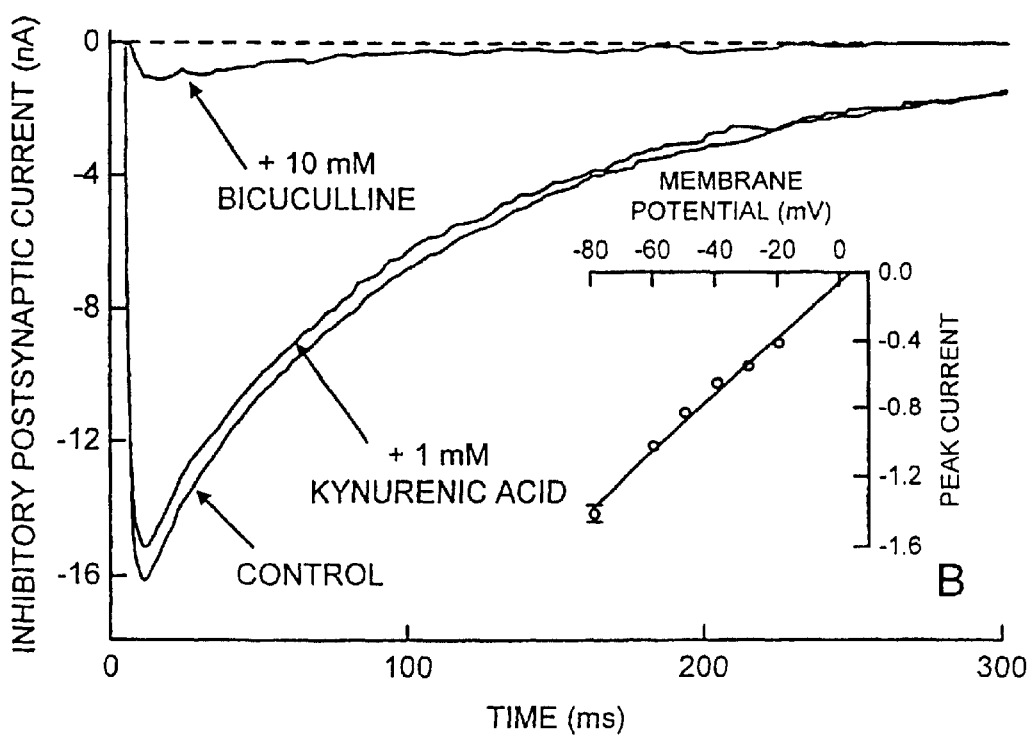

In a broad aspect, the present invention provides a method of modulating the activity of an NMDA receptor in a mammal. In particular, the invention relates to the use of xenon as an NMDA receptor antagonist.

Xenon is a chemically inert gas whose anaesthetic properties have been known for over 50 years (Lawrence J H et al, J. Physiol. 1946; 105:197–204). Since its first use in surgery (Cullen S C et al, Science 1951; 113:580–582), a number of research groups have shown it has an excellent pharmacological profile, including the absence of metabolic by-products, profound analgesia, rapid onset and recovery, and minimal effects on the cardiovascular system (Lachmann B et al, Lancet 1990; 335:1413–1415; Kennedy R R et al, Anaesth. Intens. Care 1992; 20:66–70; Luttropp H H et al, Acta Anaesthesiol. Scand. 1994; 38:121–125; Goto T et al, Anesthesiology 1997; 86:1273–1278; Marx T et al, Br. J. Anaesth. 1997; 78:326–327). However, up to now, the molecular mechanisms underlying the clinical activity of xenon have remained elusive.

We have described the use of xenon in a pharmaceutical application in United Kingdom patent application number GB 9913677.2 (filed Jun. 11, 1999), the contents of which are incorporated herein by reference.

Thus, the present invention relates to the use of xenon as an NMDA antagonist.

The term "antagonist" is used in its normal sense in the art, i.e., a chemical compound which prevents functional activation of a receptor by its natural agonist (glutamate, in this case).

It is widely known that most other anaesthetics enhance the activity of inhibitory GABA (γ-aminobutyric acid type-A) receptors (Franks N P et al Nature 1994; 367:607–614; Mihic S J et al, Nature 1997; 389:385–389). However, the effect of xenon on these receptors is believed to be negligible. Instead, xenon potently inhibits the excitatory NMDA receptor channels. This effect accounts for many of the important features of its pharmacological profile and is likely to be instrumental in the anaesthetic and analgesic effects of this inert gas.

It is to be noted that the prior art has neither disclosed nor suggested the use of xenon as an NMDA receptor antagonist.

Unlike many other NMDA antagonists, xenon is able to rapidly equilibrate with the brain by diffusing across the blood brain barrier. A further advantage of using xenon as an NMDA antagonist is that the molecule is an inert, volatile gas that can be rapidly eliminated via respiration.

In the preferred embodiment, the invention provides a method of treatment comprising modulating the activity of an NMDA receptor in a mammal, the method comprising modulating the activity of the NMDA receptor by administering to the mammal a therapeutically effective amount of xenon.

Preferably, the xenon is administered in combination with a pharmaceutically acceptable carrier, diluent or excipient. By way of example, in the pharmaceutical compositions of the present invention, xenon may be admixed with any suitable binder(s), lubricant(s), suspending agent(s), coating agent(s), solubilising agent(s) selected with regard to the intended route of administration and standard pharmaceutical practice.

The xenon may also be administered in combination with another pharmaceutically active agent. The agent may be any suitable pharmaceutically active agent including anaesthetic or sedative agents which promote GABAergic activity. Examples of such GABAergic agents include isoflurane, propofol and benzodiazapines.

Typically, the pharmaceutical compositions of the present invention may be delivered intravenously (either by bolus administration or infusion), neuraxially (either subdural or subarachnoid), transdermally, or by inhalation.

In one embodiment, the invention provides a method of treating a mammal for a condition associated with NMDA receptor activity, the method comprising modulating the activity of the NMDA receptor by administering to the mammal a therapeutically effective amount of xenon.

By way of example, the method of the present invention may be used for any one or more of the following:

a) to provide neuroprotection;

b) to relieve neuropathic pain;

c) to inhibit synaptic plasticity, e.g. to inhibit the development of tolerance to opiates.

In a second embodiment, the invention provides a method of treating a mammal for a condition associated with NMDA receptor activation, the method comprising modulating the activity of the NMDA receptor by administering to the mammal a therapeutically effective amount of xenon.

In a third embodiment, the invention provides a method of reducing the level of activation of the NMDA receptors in a mammal, the method comprising modulating the activity of the NMDA receptor by administering to the mammal a therapeutically effective amount of xenon.

A further embodiment of the invention provides a process for the preparation of a pharmaceutical composition suitable for modulating the activity of an NMDA receptor, which process comprises adding an NMDA antagonist to a pharmaceutically acceptable carrier, excipient or diluent, wherein the improvement comprises using xenon as the NMDA antagonist.

In another embodiment, the invention provides a pharmaceutical composition for modulating NMDA activity which comprises an NMDA antagonist and a pharmaceutically acceptable carrier, excipient or diluent, wherein the improvement comprises using xenon as the NMDA antagonist.

By way of example, the present invention also relates to the use of xenon in the manufacture of a medicament for any one or more of the following:

a) to provide neuroprotection;

b) to relieve neuropathic pain;

c) to inhibit synaptic plasticity, e.g. to inhibit the development of tolerance to opiates.

The concentration of xenon employed in the composition may be the minimum concentration required to achieve the desired clinical effect. It is usual for a physician to determine the actual dosage that will be most suitable for an individual patient, and this dose will vary with the age, weight and response of the particular patient. There can, of course, be individual instances where higher or lower dosage ranges are merited, and such are within the scope of this invention.

The pharmaceutical composition of the present invention may be for human administration or animal administration.

Thus, the composition of the present invention may also be used as an animal medicament. In this regard, the invention further relates to a veterinary composition comprising the composition of the present invention and a veterinarily acceptable diluent, excipient or carrier.

For veterinary use, the composition of the present invention, or a veterinarily acceptable composition thereof, is typically administered in accordance with normal veterinary practice and the veterinary surgeon will determine the dosing regimen and route of administration which will be most appropriate for a particular animal.

The invention is further described with reference to the accompanying figures wherein:

FIG. 1 shows control excitatory and inhibitory postsynaptic responses.

Figure 2:
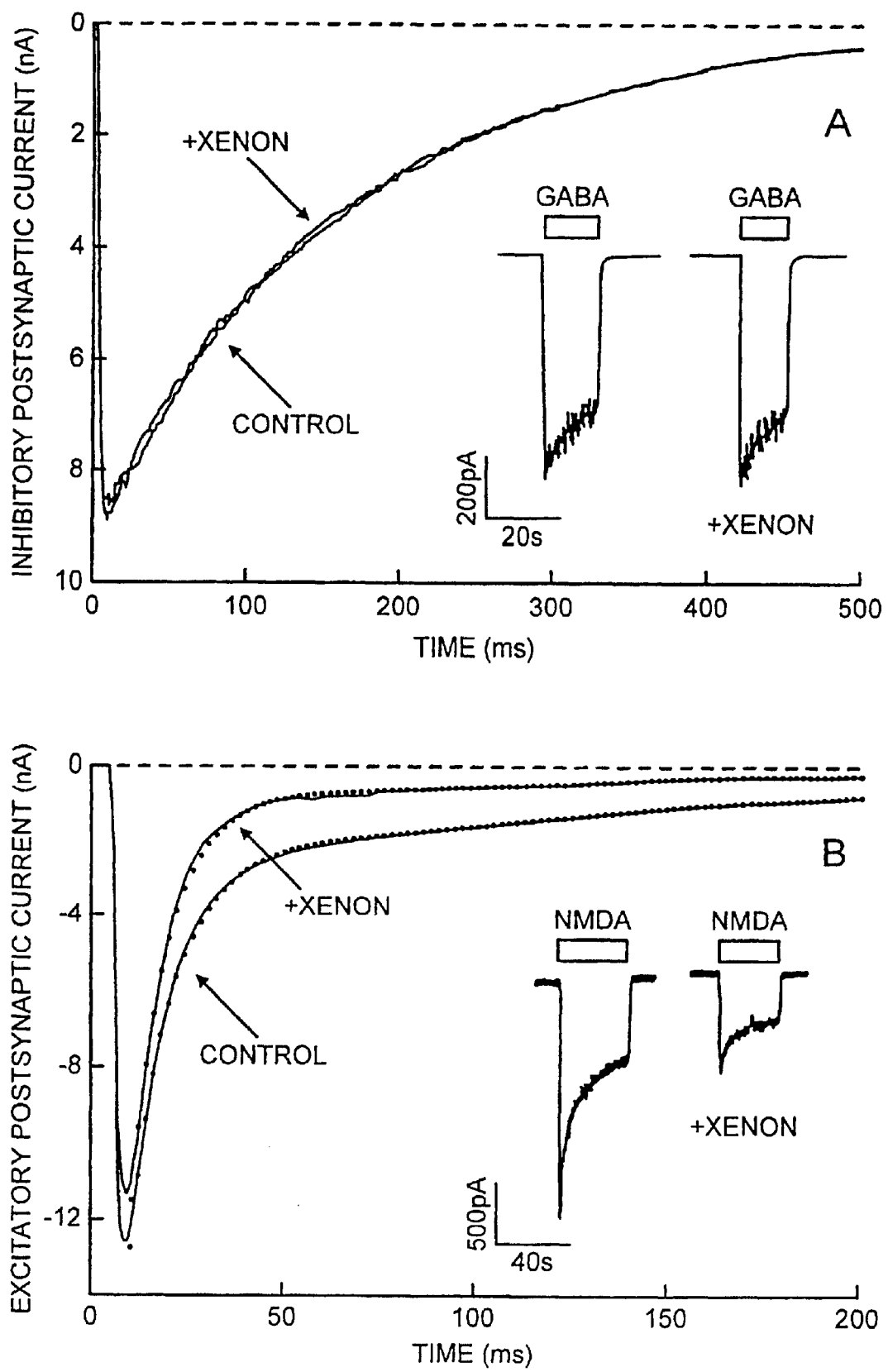
FIGS. 2A and B show representative traces illustrating the effects of xenon on inhibitory and excitatory postsynaptic responses.

FIG. 2 shows representative traces illustrating the effects of xenon on inhibitory and excitatory postsynaptic responses.

Figure 3:
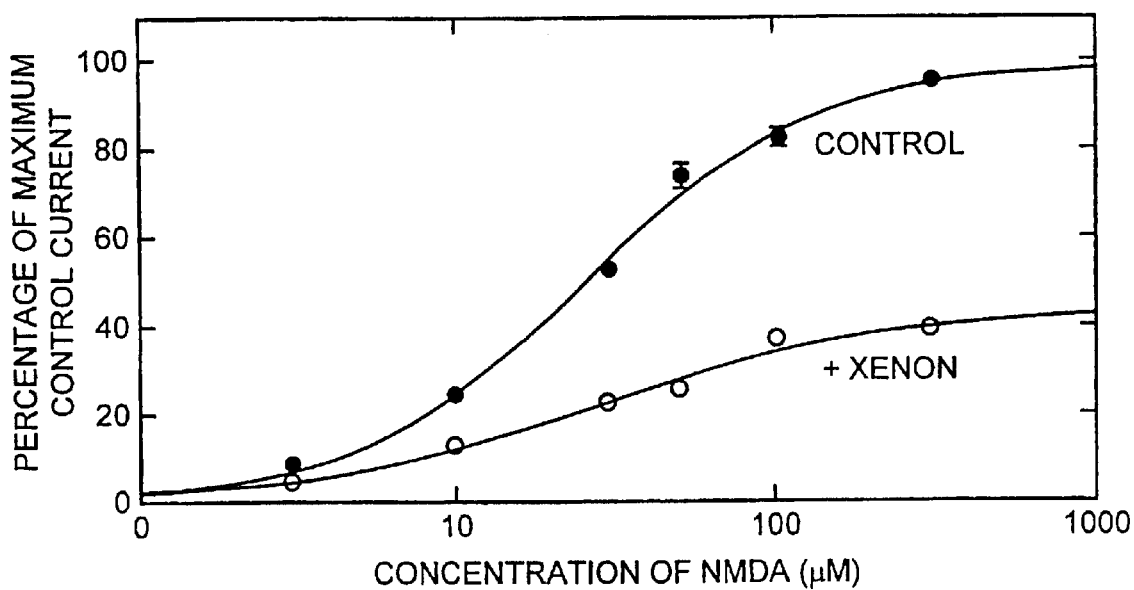
FIG. 3 shows the percentage of maximum control current against the concentration of NMDA in the presence and absence of xenon.

FIG. 3 shows the percentage of maximum control current against the concentration of NMDA in the presence and absence of xenon.

Figure 4:
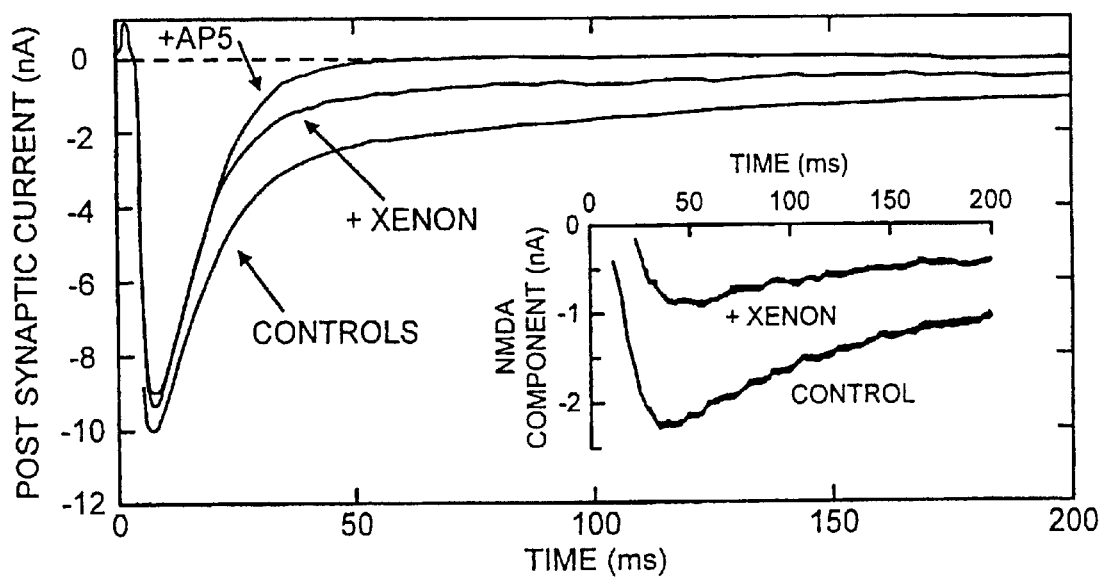
FIG. 4 shows the effect of AP5 and xenon on excitatory postsynaptic response, and inset, the NMDA-receptor-mediated component.

FIG. 4 shows the effect of AP5 and xenon on excitatory postsynaptic response, and inset, the NMDA-receptor-mediated component.

In more detail, FIG. 1 shows A) A representative excitatory postsynaptic current (EPSC) and its sensitivity to 1 mM kynurenic acid and insensitivity to 10 $\mu$M bicuculline. The inset shows the linear current-voltage relationship for the peak of the EPSC, normalized to the current measured at −60 mV; the data points represent mean values (for an average of 5 cells). B) A representative inhibitory postsynaptic current (IPSC) and its sensitivity to 10 $\mu$M bicuculline and insensitivity to 1 mM kynurenic acid. The inset shows the linear current-voltage relationship for the peak of the IPSC, normalized to the current measured at −60 mV; the data points represent mean values (for an average of 6 cells). In the insets the errors bars are SEMs, but these are not shown where they are smaller than the size of the symbol.

In more detail, FIG. 2 shows A) GABAergic postsynaptic currents in the presence and absence of 3.4 mM xenon. Xenon has no significant effect on the IPSC. The inset shows representative traces illustrating the lack of an effect of 4.3 mM xenon on the current evoked by 3 $\mu$M GABA. B) Glutamatergic postsynaptic currents in the presence and absence of 3.4 mM xenon. The principal effect is a reduction in the slow component of the current (in this example by about 70%). The dots represent biexponential fits to the measured currents. The inset shows representative traces illustrating the effect of 3.4 mM xenon on the current evoked by 100 $\mu$M NMDA. In more detail, FIG. 3 shows that NMDA activates an inward current (in neurons clamped at −60 mV) with an $EC_{50}$ of 24±2 $\mu$M NMDA and a Hill coefficient of 1.2±0.1. Xenon inhibits the current by approximately 60% but does not significantly change either the $EC_{50}$ or the Hill coefficient. Each data point represents the mean peak current from at least 6 cells.

In more detail, FIG. 4 shows that xenon selectively inhibits the NMDA-receptor-mediated component of glutamatergic excitatory postsynaptic currents (EPCSs). Neurons were voltage-clamped at −60 mV; synaptic responses were stimulated by a 2-ms depolarising pulse to +20 mV. Control glutamatergic EPSCs displayed a characteristic biphasic decay. The slow component was completely blocked by 200 μM AP5, leaving the fast component almost unaffected. Inset, the NMDA-receptor-mediated component (the difference between the control EPCS and that in the presence of AP5) and its size in the presence of xenon (calculated by taking the difference between the EPSC in the presence of xenon and that in the presence of AP5). Control solutions were equilibrated at room temperature with 80% $N_2$ and 20% $O_2$, and the test solutions with 80% xenon and 20% $O_2$.

Studies carried out by the applicant have shown that xenon has virtually no effect on $GABA_A$ receptors. Currents activated by 3 μM GABA, both in voltage-clamped cultured rat hippocampal neurons and in voltage-clamped PA3 cells (Hadingham K L et al, Proc. Natl. Acad. Sci. USA, 1992; 89, 6378–6382) that stably expressed defined GABA subunits, were not significantly affected, even by 100% xenon. The significance of this observation becomes apparent, given that in order to function as a human anaesthetic, the half maximal effective concentration $EC_{50}$ is 71% v/v (Cullen et al, Anesthsiology 1969, 305–309). Xenon was also shown to have little effect on functional GABA-releasing synapses in hippocampal neurons, with 80% xenon reducing peak inhibitory post-synaptic currents by only 8±2%, indicating that the presynaptic effects of xenon must be very modest.

In contrast, xenon was shown to have a significant effect on NMDA receptors. Mechanistic studies on cultured hippocampal neurons have shown that 80% xenon, (which will maintain surgical anaesthesia) reduces NMDA-activated currents by up to 60%, with no significant change in the NMDA $EC_{50}$ value or Hill coefficient. This non-competitive inhibition indicates that xenon should strongly inhibit neural transmission, despite the high glutamate concentrations in synaptic clefts.

Further studies were carried out using microisland cultures of hippocampal neurons that form synapses with themselves (autapses) (Bekkers J M et al, Proc. Natl. Acad. Sci. USA, 1991; 88, 7834–7838). A typical glutarnatergic postsynaptic current recorded from a hippocampal neuron is shown in FIG. 4. The control records show a characteristic biphasic time course, with a fast component mediated by non-NMDA receptors and a much slower component mediated by NMDA receptors. The NMDA receptor mediated component is readily identified as it is blocked by the highly selective competitive antagonist AP5, DL-2-amino-5-phosphononpentanoate (Watkins J C et al, Annu. Rev. Pharmacol. Toxicol. 1981; 21, 165–204).

Addition of 200 μM AP5 was shown to almost completely block the slow component, leaving only a fast component, with a single exponential time course very similar to that of the control fast component. The effect of xenon on the glutamatergic postsynaptic current resembles that of AP5 (FIG. 4). The slow NMDA-receptor-mediated component is reduced by over 70%, whereas the fast component barely changes. So, not only does xenon inhibit synaptic NMDA receptors, it has little apparent effect on non-NMDA receptors.

In terms of the effect on synaptic currents, the selectivity of action observed with xenon is unexpected. In view of the fact that almost all general anaesthetics potentiate the actions of GABA at GABAA receptors (Tanelian D L et al, Anesthesiology 1993, 78:757–776; Franks N P et al, Nature 1994; 367:607–614), it was anticipated that xenon would be no exception. However, the complete absence of an effect of xenon on $GABA_A$ receptors puts it into the same class of agents as ketamine, a so-called "dissociative" anaesthetic, which is also ineffective at $GABA_A$ receptors (Brockmeyer D M er al, Br. J. Anesesth. 1995; 74:79–84) and is thought to act predominantly at NMDA receptors. Similarly, results have shown that xenon selectively blocks NMDA receptors with little effect at AMPA/KA receptors. This latter result strongly suggests that the actions of xenon are postsynaptic in origin. The lack of an effect of xenon on the decay time of the NMDA receptor component, however, rules out a simple open channel block mechanism of inhibition, as does the observation that the $EC_{50}$ concentration for NMDA-evoked currents does not change in the presence of xenon. Whatever the exact molecular basis for the surprising selectivity of xenon for NMDA receptors, it rather simply accounts for many features of its unusual pharmacological profile, including the ability to induce profound analgesia and psychotomimetic effects.

It is thus clear that xenon is surprisingly selective in its action, having very different effects on excitatory and inhibitory synaptic transmission. The action of xenon may be accounted for solely in terms of effects at glutamatergic synapses, although other targets may well be identified in the future. Nonetheless, the insensitivity of GABAergic synapses to xenon indicates that its mechanisms of action are clearly different to those of most general anaesthetics. At the mechanistic level, it is clear that for xenon, postsynaptic receptors are the most important molecular targets.

The present invention is further described by way of example.

EXAMPLE

Culturing Hippocampal Neurons

Hippocampal neurons were grown in culture using methods described previously (Segal M M et al, J. Neurophysiol. 1990, 64:1390–1399; Bekkers J M et al, Proc. Natl. Acad. Sci. U.S.A. 1991, 88:7834–7838; Mennerick S et al, J. Neurophysiol. 1995, 73:320–332). Briefly, hippocampi from Sprague Dawley rats (postnatal day 1–3) were dissected, roughly sliced and agitated in a papain-containing solution (20 units $ml^{-1}$) for 30 minutes at 37EC. After washing with enzyme-free solution, the tissue was gently triturated with a fire-polished Pasteur pipette and the cells were plated out at a density of 8–10×$10^4$ cells ml and cultured (95% air/5% $CO_2$) at 37° C. Glass coverslips used for culturing the cells were first coated with agarose (0. 15% w/v) and then sprayed with a fine mist of poly-D-lysine (PDL) and collagen (0.1 mg $ml^{-1}$ PDL and 0.5 mg $ml^{-1}$ rat-tail collagen) from a glass micro-atomiser and sterilized by UV exposure. This produced micro-islands of permissive substrate with diameters of between 100 and 1000 μm. At 3–4 days after plating, when the glial cell layer was about 80% confluent, an anti-mitotic agent (cytosine β-D-arabinofuranoside, 5 μM) was added to arrest glial cell proliferation. Neuronal cultures were then allowed to mature for another 4–9 days. We used micro-islands which contained single isolated neurons whose axonal processes and dendritic trees formed multiple self-synapses (autapses). This procedure provided a large population of phenotypically identical monosynaptic connections.

Electrophysiology

The neurons were voltage-clamped using the whole-cell recording technique (Axopatch 200 amplifier, Axon Instruments, Foster City, Calif.). Electrodes were fabricated from borosilicate glass and typically had resistances of between 3–5 MΩ. Series resistance was compensated by 75–90%. Neurons were voltage-clamped at −60 mV, and synaptic responses were stimulated by a 2 ms depolarising pulse to +20 mV. Shortly after the restoration of the membrane potential to −60 mV, a large (1–20 nA) postsynaptic current was observed and recorded. For the synaptic measurements, data were sampled at 50 kHz, filtered at 20 kHz (−3 dB, 8-pole Bessel) and stored on a computer. The extracellular recording solution was (mM) 137 NaCl, 5 KCl, 3 CaCl$_2$, 5 HEPES, 10 glucose, 0.001 glycine, 0.0001 strychnine-HCl, titrated to pH 7.3 with NaOH; and the intracellular (pipette) solution was (mM) 140 KCl, 4 NaCl, 0.5 EGTA, 2 MgATP, 10 HEPES, titrated to pH 7.25 with KOH.

For the experiments where GABA, NMDA or glutamate were exogenously applied, the neurons were grown in mass culture and used 3–11 days after plating. Data were sampled at 200 Hz and filtered at 100 Hz (−3 dB, 8-pole Bessel). The extracellular recording solution for NMDA- and glutamate-evoked responses was (mM) 150 NaCl, 4 KCl, 2 CaCl$_2$, 10 HEPES, 10 glucose, 0.0002 tetrodotoxin citrate (Tocris Cookson, Bristol, UK), 0.1 picrotoxin, 0.0001 strychnine-HCl, 0.001 glycine, titrated to pH 7.40 with NaOH; the extracellular recording solution for GABA-evoked responses was (mM) 150 NaCl, 4 KCl, 1 CaCl$_2$, 1 MgCl$_2$, 10 HEPES, 10 glucose, 0.0002 tetrodotoxin citrate, titrated to pH 7.40 with NaOH; and the intracellular (pipette) solution for GABA-, NMDA- and glutamate-evoked responses was (mM) 140 CsCl, 3 NaCl, 11 EGTA, 2 MgATP, 10 HEPES, titrated to pH 7.20 with CsOH. Unless otherwise stated, all chemicals were obtained from Sigma Chemical Co. (Poole, Dorset, UK). Test solutions were applied to the cells using a rapid-switching perfusion system (Downie D L et al, Br. J. Pharmacol. 1996, 118:493–502). All electrophysiological measurements were carried out at room temperature (20–23° C.).

Preparation of Anaesthetic Solutions

Xenon solutions were prepared by first bubbling pure gases (oxygen, nitrogen or xenon) through fine sintered-glass bubblers in 250- or 500-ml Drechsel bottles filled with extracellular recording saline. Solutions were bubbled for 1.5–2 hours, although equilibrium was found to occur within 45 minutes. (To minimise oxidization, the neurotoxins and neurotransmitters were excluded from the fully oxygenated saline.) During bubbling, the solutions were continually stirred at room temperature. These solutions were then mixed to achieve the desired final concentrations of the gases. Our control solutions usually contained 80% of the nitrogen solution and 20% of the oxygen solution, while our test solutions usually contained 80% of the xenon solution and 20% of the oxygen solution. Using a Bunsen water/gas partition coefficient of 0.0965 (Smith R A et al, Biochim. Biophys. Acta 1981, 645:327–338) we calculate that our standard test solution contained 3.4 mM xenon. Xenon (research grade, 99.993% pure) was supplied by BOC gases, Guildford, Surrey, UK. In all cases xenon was pre-applied to the neurons for at least 30 seconds before the initiation of synaptic currents.

Integration of the Synaptic Responses

In order to obtain an estimate for the total charge transfer, the EPSCs or IPSCs were numerically integrated. However, because in some cases the currents had not decayed to baseline by the end of the recording period, a correction (which was invariably less than 5% of the total charge transfer) was applied by extrapolating the observed current to the baseline using a biexponential fit to the decay phase of the response.

Control Synaptic Currents

The control synaptic currents were characterized and almost invariably fell into one of two populations, in accordance with the findings of previous studies (Bekkers J M et al, Proc. Natl. Acad. Sci. U.S.A. 1991, 88:7834–7838; Mennerick S et al, J. Neurophysiol. 1995, 73:320–332). Approximately half of the cells exhibited postsynaptic currents which decayed relatively rapidly (~8 ms half-time), while the other half exhibited currents that were markedly slower (~40 ms half-time) (see FIG. 1 and Table 1). The more rapid responses were recorded from cells with a rounded appearance and complex dendritic trees. Their sensitivity to kynurenic acid (80±3% inhibition of the peak current with 1 mM kynurenic acid; n=7 cells) and insensitivity to bicuculline (0.4±1.3% inhibition of the peak current with 10 μM bicuculline; n=13 cells) identifies these cells as excitatory glutamatergic neurons. In contrast, the slower synaptic currents were almost completely blocked by bicuculline (94±1% inhibition of the peak current with 10 μM bicuculline; n=8 cells) and unaffected by kynurenic acid (6±4% inhibition of the peak current with 1 mM kynurenic acid; n=5 cells), thus identifying these responses as GABAergic. These inhibitory neurons tended to be flatter, with simpler dendritic trees. Because of the recent finding that GABA and glycine can be co-released by spinal-cord interneurons (Jonas P et al, Science 1998, 281:419–424), we considered the possibility that the inhibitory responses we were recording were mediated, in part, by glycine receptors. However, the control current was barely affected (4±2% inhibition; n=6 cells) by 100 nM strychnine, confirming that the inhibitory currents were entirely GABAergic.

The excitatory and inhibitory currents had essentially identical rise-times (see Table 1), and the peaks of the currents changed linearly with test potential (see insets to FIG. 1). The decay phase of the synaptic current I(t), where t is the time measured from the peak of the current, was fit by a biexponential equation of the form $$I(t) = I_{fast} e^{-t/\tau_{fast}} + I_{slow} e^{-t/\tau_{slow}}$$

where $I_{fast}$ and $I_{slow}$ are the amplitudes and $\tau_{fast}$ and $\tau_{slow}$ are the time constants of the fast and slow components, respectively. The values for these decay time constants measured from control excitatory and inhibitory responses are given in Table 1. In both cases, approximately two-thirds of the total charge transfer was carried by the slow component. For the excitatory glutamatergic responses, this slow component can be readily identified as being mediated by NMDA receptors because it is completely (99±1%; n=10 cells) blocked by 200 μM AP5 (DL-2-amino-5-phosphonopentanoate), a highly selective NMDA receptor antagonist (Davies J et al, Neurosci. Letts 1981, 21:77–81). In the presence of this concentration of AP5 the decay phase of the synaptic current could be fitted well by a single exponential with magnitude and time course little different to those of the control fast component. This fast component, which very largely determines the magnitude of the peak excitatory current ($I_{fast}/I_{total}$=99±1%; n=13 cells), can be attributed to currents mediated by AMPA/KA receptors (Bekkers J M et al, Proc. Natl. Acad. Sci. U.S.A. 1991, 88:7834–7838; Mennerick S et al, J. Neurophysiol. 1995, 73:320–332).

The Effects of Xenon on Synaptic Currents

The gaseous concentration of xenon which prevents a response to a painful stimulus (i.e. MAC) appears to vary among species, being 71% atm in humans (Cullen S C et al, Anesthesiology 1969, 31:305–309), 98% atm in rhesus monkeys (Whitehurst S L et al, J. Neurosurg. Anesthesiol. 1994, 6:275–279) and 161 % atm in rats (Koblin D D et al, Anesth. Analg. 1998, 87:419–424). When these values are converted to free aqueous concentrations at 37° C (Franks N P et al, Br. J. Anaesth. 1993, 71: 65–76; Franks N P et al, Anesthesiology, 1996, 84:716–720) using an Ostwald water/gas partition coefficient of 0.0887 (Weathersby P K et al, Undersea Biomed. Res. 1980, 7:277–296), the values obtained are 2.5 mM, 3.4 mM and 5.6 mM for humans. monkeys and rats respectively, with the average value being 3.8 mM. For the experiments described herein, performed at room temperature, the concentration of xenon present in the standard test solution was 3.4 mM. At this concentration, xenon had negligible effects on the inhibitory synaptic currents but strongly depressed the excitatory currents. This is illustrated with representative traces in FIG. 2.

For the GABAergic synaptic currents, 3.4 mM xenon affected neither the peak value. nor the time course of the postsynaptic currents. Percentage changes in the various inhibitory synaptic parameters are listed in Table 2, where it can be seen that none were significantly changed. The effects of xenon on currents evoked by a low (3 $\mu$M) concentration of exogenously applied GABA were also investigated. Here, 4.3 mM xenon had no significant effect on the GABA-induced current (2±3% potentiation, n=4 cells). A representative pair of traces is shown in the inset to FIG. 2A. In contrast, 3.4 mM xenon greatly depressed the glutamatergic synaptic current, with the effect being confined, almost exclusively, to the slow NMDA receptor-mediated component of the current (FIG. 2B). This is evident in the percentage changes in the various excitatory synaptic parameters which are listed in Table 2. Here it can be seen that the qualitative effects of xenon are remarkably closely mimicked by the effects of AP5. At the given concentration of AP5 (200 $\mu$M), the NMDA receptor component would be expected to be almost completely blocked (Davies J et al, Neurosci. Letts 1981, 21:77–81), and this is consistent with the 99% block of $I_{slow}$ (see Table 2). This is accompanied by a 75% reduction in total charge transfer, close to the 61% of the total charge which we estimate to be carried by the slow NMDA receptor-mediated component (see Table 1). The difference may be accounted for by the small, but significant reduction of the fast time constant $\tau_{fast}$ by AP5 (Table 2). Xenon, likewise, causes a large inhibition (70%) of $I_{slow}$ and a large inhibition (56%) of the total charge transfer, with only a small effect on the fast AMPA/KA receptor-mediated component.

Modifications to the present invention will be apparent to those skilled in the art. The references mentioned herein are incorporated herein by reference.

TABLE 1

Control parameters for synaptic currents.

| Parameter | Excitatory currents | n[a] | Inhibitory currents | n[a] |
|---|---|---|---|---|
| Time to peak (ms) | 4.9 ± 0.6 | 12 | 5.0 ± 0.3 | 14 |
| Decay half-time (ms) | 7.8 ± 0.5 | 13 | 38.5 ± 3.5 | 16 |
| $\tau_{fast}$ (ms) | 9.0 ± 0.7 | 13 | 38.1 ± 3.9 | 16 |
| $\tau_{slow}$ (ms) | 210 ± 28 | 13 | 229 ± 44 | 16 |
| $I_{fast}/I_{total}$[b] | 0.92 ± 0.01 | 13 | 0.70 ± 0.04 | 17 |
| $Q_{slow}/Q_{total}$[c] | 0.61 ± 0.04 | 13 | 0.63 ± 0.04 | 16 |

[a] number of cells
[b] $I_{total} = I_{fast} + I_{slow}$
[c] $Q_{total} = Q_{fast} + Q_{slow}$

TABLE 2

The effects of 3.4 mM (~1 MAC) xenon on synaptic currents and of 200 $\mu$M AP5 on excitatory synaptic currents

| | Inhibitory currents | | | Excitatory currents | | | | | |
|---|---|---|---|---|---|---|---|---|---|
| | +3.4 mM xenon | | | +3.4 mM xenon | | | +200 $\mu$M AP5 | | |
| Parameter | % change (means ± SEM) | ↑, ↓ or ns[a] | n[b] | % change (means ± SEM) | ↑, ↓ or ns[a] | n[b] | % change (means ± SEM) | ↑, ↓ or ns[a] | n[b] |
| $I_{peak}$ | -3.1 ± 2.2 | ns | 11 | -13.5 ± 1.8 | ↓ | 10 | -16.3 ± 2.1 | ↓ | 10 |
| Decay half-time | -3.4 ± 2.4 | ns | 10 | -22.7 ± 2.5 | ↓ | 11 | -24.1 ± 3.3 | ↓ | 10 |
| Total charge transfer | -2.3 ± 3.9 | ns | 10 | -55.6 ± 2.7 | ↓ | 11 | -75.2 ± 2.5 | ↓ | 10 |
| $I_{fast}$ | -4.3 ± 2.8 | ns | 11 | -4.1 ± 5.2 | ns | 11 | 6.8 ± 6.2 | ns | 10 |
| $I_{slow}$ | 18.8 ± 12.4 | ns | 11 | -70.3 ± 2.4 | ↓ | 11 | -98.8 ± 0.8 | ↓ | 10 |
| $\tau_{fast}$ | -1.3 ± 3.5 | ns | 11 | -12.3 ± 1.8 | ↓ | 11 | -5.9 ± 2.3 | ↓ | 10 |
| $\tau_{slow}$ | 0.8 ± 6.0 | ns | 11 | -6.7 ± 6.5 | ns | 11 | — | — | — |
| $Q_{fast}$ | 1.5 ± 7.2 | ns | 12 | -11.4 ± 5.6 | ns | 11 | 5.3 ± 9.6 | ns | 10 |
| $Q_{slow}$ | 12.6 ± 8.4 | ns | 12 | -68.2 ± 4.2 | ↓ | 11 | -96.0 ± 3.4 | ↓ | 10 |

[a] not significant at the 95% confidence level (Student's t-test)
[b] number of cells

What is claimed is:

1. A method for providing neuroprotection, relieving neuropathic pain, or inhibiting synaptic plasticity in a mammal comprising administering to a mammal in need thereof xenon in an amount effective to modulate the activity of an NMDA receptor in said mammal.

2. A method according to claim 1 which provides neuroprotection in the mammal.

3. A method according to claim 1 which relieves neuropathic pain in the mammal.

4. A method according to claim 1 which inhibits synaptic plasticity in the mammal.

5. A method according to claim 1 wherein the xenon is administered in combination with a pharmceutically acceptable carrier, diluent or excipient.

6. A method according to claim 1 wherein the mammal is treated for a condition associated with NMDA receptor activation.

7. A method according to claim 1 wherein the mammal is treated for a condition associated with NMDA receptor activity.

8. A method according to claim 1 further comprising administering to the mammal an anaesthetic or sedative agent that promotes GABAergic activity.

9. A method according to claim 8 wherein the agent that promotes GABAergic activity is selected from the group consisting of isoflurane, propofol, a benzodiazapine, and mixtures thereof.

10. A method according to claim 1 which inhibits the development of tolerance to opiates.

* * * * *